(12) United States Patent
Lin

(10) Patent No.: US 6,812,366 B2
(45) Date of Patent: Nov. 2, 2004

(54) CATALYST USEFUL FOR OXIDATION REACTIONS

(75) Inventor: Manhua Lin, Maple Glen, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 10/653,634

(22) Filed: Sep. 2, 2003

(65) Prior Publication Data

US 2004/0054223 A1 Mar. 18, 2004

Related U.S. Application Data

(62) Division of application No. 09/677,389, filed on Oct. 2, 2000, now Pat. No. 6,653,253.
(60) Provisional application No. 60/157,283, filed on Oct. 1, 1999.

(51) Int. Cl.[7] .................. C07C 45/34; C07C 27/10; C07C 51/10
(52) U.S. Cl. ............ 568/470; 568/476; 568/477; 568/478; 562/512.2; 562/518; 562/522
(58) Field of Search ............... 568/470, 476, 568/477, 478; 562/512.2, 518, 522

(56) References Cited

U.S. PATENT DOCUMENTS

| 3,936,505 | A | | 2/1976 | Oda et al. ............. 260/604 |
|---|---|---|---|---|
| 5,198,580 | A | | 3/1993 | Bartek et al. .......... 562/542 |
| 5,380,933 | A | | 1/1995 | Ushikubo et al. ....... 562/545 |
| 5,602,280 | A | * | 2/1997 | Nagai et al. ........... 562/546 |
| 5,892,108 | A | * | 4/1999 | Shiotani et al. ........ 562/532 |
| 6,084,126 | A | * | 7/2000 | Hibst et al. ........... 562/535 |
| 6,180,825 | B1 | * | 1/2001 | Lin et al. ............. 562/549 |
| 6,514,903 | B2 | * | 2/2003 | Lin et al. ............. 502/311 |
| 6,693,059 | B2 | * | 2/2004 | Lin .................... 502/308 |
| 6,710,207 | B2 | * | 3/2004 | Bogan et al. .......... 562/549 |

FOREIGN PATENT DOCUMENTS

| EP | 0 529 853 | 3/1993 |
|---|---|---|
| EP | 0 962 253 | 12/1999 |

* cited by examiner

*Primary Examiner*—Johann Richter
*Assistant Examiner*—Sikarl A. Witherspoon

(57) ABSTRACT

A catalyst useful for oxidation reactions is disclosed. The catalyst is useful for the gas phase oxidation of alkanes, propylene, acrolein, or isopropanol to unsaturated aldehydes or carboxylic acids.

9 Claims, 1 Drawing Sheet

CATALYST USEFUL FOR OXIDATION REACTIONS

CROSS REFERENCE TO RELATED PATENT APPLICATIONS

Figure 1:
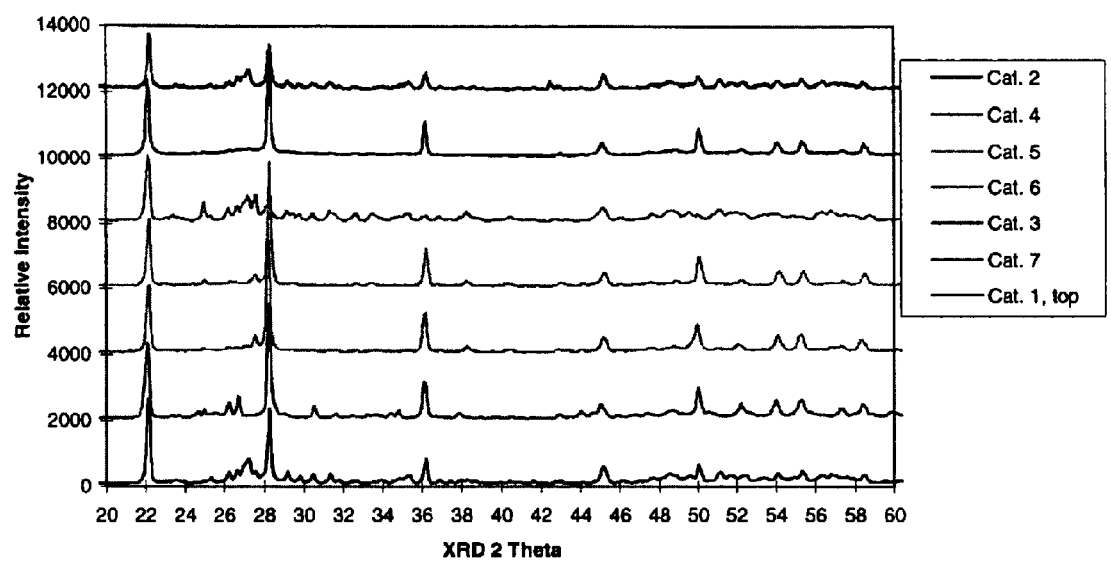

This non-provisional application is a divisional non-provisional U.S. patent application Ser. No. 09/677,389 filed Oct. 2, 2000, now U.S. Pat. No. 6,653,253,; benefit of which is claimed under 35 U.S.C. §120 and which in turn claims benefit under 35 U.S.C. §119(e) of U.S. provisional Application No. 60/157,283 filed Oct. 1, 1999, priority benefit of which is also claimed for the present divisional application.

This invention relates to a catalyst which is useful for oxidation reactions. In particular, the invention relates to a catalyst which is efficient in converting alkanes, alkenes, or alcohols to unsaturated aldehydes and acids, and a process for preparing unsaturated aldehydes and acids using the catalyst.

Unsaturated aldehydes and acids are important commercial chemicals. Of particular importance is (meth)acrylic acid. The highly reactive double bond and acid function of (meth)acrylic acid makes it especially suitable as a monomer which may be polymerized alone or with other monomers to produce commercially important polymers. These unsaturated acids are also useful as a starting material for esterification to produce commercially important (meth)acrylate esters. Materials derived from (meth)acrylic acid or esters of (meth)acrylic acids are useful as plastic sheets and parts, paints and other coatings, adhesives, caulks, sealants, plastic additives, and detergents as well as other applications.

The production of unsaturated acids by oxidation of an olefin is well known in the art. Acrylic acid, for instance, may be commercially manufactured by the gas phase oxidation of propylene. It is also known that unsaturated carboxylic acids may also be prepared by oxidation of alkanes. For instance, acrylic acid may be prepared by the oxidation of propane. Such a process is especially desirable because alkanes generally have a lower cost than olefins. For example, at the time of filing this application propylene costs approximately three times more than propane. A suitable economic process for the oxidation of alkanes, as well as from oxidation of starting materials, to unsaturated aldehydes which is commercially viable has yet to be achieved.

There is continuing research in the area of new catalysts and starting materials for the production of (meth)acrylic acid and (meth)acrolein. This research generally is directed at reducing the cost of raw materials or increasing the yield of the oxidation process.

One impediment for the production of a commercially viable process for the catalytic oxidation of an alkane to an unsaturated acid is the identification of a catalyst having adequate conversion and suitable selectivity, thereby providing sufficient yield of the unsaturated acid end-product. U.S. Pat. No. 5,380,933 discloses a method for preparing a catalyst useful in the gas phase oxidation of an alkane to an unsaturated carboxylic acid. In the disclosed method, a catalyst was prepared by combining ammonium metavanadate, telluric acid and ammonium paramolybdate to obtain a uniform aqueous solution. To this solution was added ammonium niobium oxalate to obtain a slurry. The water was removed from the slurry to obtain a solid catalyst precursor. The solid catalyst precursor was molded into a tablet, sieved to a desired particle size and then calcined at 600° C. under a nitrogen stream to obtain the desired catalyst.

Co-pending U.S. patent application Ser. No. 09/316,007 disclosed a process for preparing a catalyst for catalyzing an alkane into an unsaturated aldehyde or carboxylic acid wherein phase segregation was minimized and improvement in selectivity, conversion, and yield were achieved.

Despite the disclosure of the references, there is a continuing need for new catalysts and improved processes for the production of (meth)acrylic acid and/or (meth)acrolein.

In one aspect of the present invention, there is provided a catalyst having the formula:

wherein $0.25<a<0.98$, $0.003<m<0.5$, $0.003<n<0.5$, $0.003<x<0.5$, and o is dependent on the oxidation state of the other elements, and A is at least one of Mo, W, Fe, Nb, Ta, Zr, and Ru; M is at least one of V, Ce, and Cr; N is at least one of Te, Bi, Sb, and Se; and X is at least one of Nb, Ta, W, Ti, Al, Zr, Cr, Mn, Fe, Ru, Co, Rh, Ni, Pd, Pt, Sb, Bi, B, In, and Ce; wherein the catalyst exhibits at least two crystal phases, one phase including major x-ray diffraction peaks at 22.1, 28.2, 36.2, 45.2, 50.5, 54.2, 55.4, and 58.5, and a second phase including major x-ray diffraction peaks at 22.1, 27.2, 35.3, 45.2, and 51.1.

In a second aspect of the present invention, there is provided a process for preparing unsaturated aldehydes and acids including subjecting an alkane to catalytic oxidation in the presence of a catalyst having the formula

wherein $0.25<a<0.98$, $0.003<m<0.5$, $0.003<n<0.5$, $0.003<x<0.5$, and o is dependent on the oxidation state of the other elements, and A is at least one of Mo, W, Fe, Nb, Ta, Zr, and Ru; M is at least one of V, Ce, and Cr; N is at least one of Te, Bi, Sb, and Se; and X is at least one of Nb, Ta, W, Ti, Al, Zr, Cr, Mn, Fe, Ru, Co, Rh, Ni, Pd, Pt, Sb, Bi, B, In, and Ce; wherein the catalyst exhibits at least two crystal phases, one phase including major x-ray diffraction peaks at 22.1, 28.2, 36.2, 45.2, 50.5, 54.2, 55.4, and 58.5, and a second phase including major x-ray diffraction peaks at 22.1, 27.2, 35.3, 45.2, and 51.1.

In a third aspect, the present invention provides a process for preparing unsaturated aldehydes and acids including subjecting a compound selected from propylene, acrolein, and isopropanol to catalytic oxidation in the presence of a catalyst having the formula:

wherein $0.25<a<0.98$, $0.003<m<0.5$, $0.003<n<0.5$, $0.003<x<0.5$, and o is dependent on the oxidation state of the other elements, and A is at least one of Mo, W, Fe, Nb, Ta, Zr, and Ru; M is at least one of V, Ce, and Cr; N is at least one of Te, Bi, Sb, and Se; and X is at least one of Nb, Ta, W, Ti, Al, Zr, Cr, Mn, Fe, Ru, Co, Rh, Ni, Pd, Pt, Sb, Bi, B, In, and Ce; wherein the catalyst exhibits at least two crystal phases, one phase including major x-ray diffraction peaks at 22.1, 28.2, 36.2, 45.2, 50.5, 54.2, 55.4, and 58.5, and a second phase including major x-ray diffraction peaks at 22.1, 27.2, 35.3, 45.2, and 51.1.

FIG. 1 depicts the x-ray diffraction (XRD) spectra of major XRD peaks for catalysts 1–7.

As used herein, the expression "(meth)acrylic acid" is intended to include both methacrylic acid and acrylic acid within its scope. In a like manner, the expression "(meth)acrylates" is intended to include both methacrylates and acrylates within its scope and the expression "(meth)acrolein" is intended to include both acrolein and methacrolein within its scope.

As used herein the terminology "($C_3$–$C_8$) alkane" means a straight chain or branched chain alkane having from 3 to 8 carbon atoms per alkane molecule.

As used herein the term "mixture" is meant to include within its scope all forms of mixtures including, but not limited to, simple mixtures as well as blends, alloys, etc.

For purposes of this application "% conversion" is equal to (moles of consumed alkane/moles of supplied alkane)×100; "% selectivity" is equal to (moles of formed desired unsaturated carboxylic acid or aldehyde/moles of consumed alkane)×100; and "% yield" is equal to (moles of formed desired unsaturated carboxylic acid or aldehyde/moles of supplied alkane)×(carbon number of formed desired unsaturated carboxylic acid or aldehyde/carbon number of the supplied alkane)×100.

For purposes of this application by "solution" is meant that greater than 95 percent of metal solid added to a solvent is dissolved. It is to be understood that the greater the amount of metal solid not initially in solution, the poorer the performance of the catalyst derived therefrom will be.

As recited above, a catalyst having at least two specific crystal phases is disclosed. The two crystal phases may be obtained either through a specific method of preparation of the catalyst or through varying the composition of the catalyst.

In a first step of the method of preparation of the catalyst, a solution is formed by admixing metal compounds, at least one of which contains oxygen, and at least one solvent in appropriate amounts to form the solution. Generally, the metal compounds contain elements A, M, N, X, and O. In one embodiment, A is at least one of Mo, W, Fe, Nb, Ta, Zr, and Ru; M is at least one of V, Ce, and Cr; N is at least one of Te, Bi, Sb, and Se; and X is at least one of Nb, Ta, W, Ti, Al, Zr, Cr, Mn, Fe, Ru, Co, Rh, Ni, Pd, Pt, Sb, Bi, B, In, and Ce. In a preferred embodiment, A is at least one of Mo and W; M is at least one of V, Ce, and Cr; N is at least one of Te, Bi, and Sb; and X is at least one of Nb, Ta, and Zr. In a more preferred embodiment, A is Mo, M is V, N is Te and X is Nb.

Suitable solvents include water, alcohols including, but not limited to, methanol, ethanol, propanol, and diols etc, as well as other polar solvents known in the art. Generally, water is preferred. The water is any water suitable for use in chemical synthesis including, without limitation, distilled water and deionized water. The amount of water present is that amount sufficient to keep the elements substantially in solution long enough to avoid or minimize compositional and/or phase segregation during the preparation steps. Accordingly, the amount of water will vary according to the amounts and solubility of materials combined. However, as stated above the amount of water must be sufficient to insure an aqueous solution is formed and not a slurry at the time of mixing.

Once the aqueous solution is formed, the water is removed by a combination of any suitable methods known in the art to form a catalyst precursor. Such methods include, without limitation, vacuum drying, freeze drying, spray drying, rotary evaporation, and air drying. Vacuum drying is generally performed at pressures ranging from 10 to 500 mm/Hg. Freeze drying typically entails freezing the solution, using for instance liquid nitrogen, and drying the frozen solution under vacuum. Spray drying is generally performed under an inert atmosphere such as nitrogen, argon, or air with an inlet temperature ranging from 125° C. to 200° C. and an outlet temperature ranging from 75° C. to 150° C. Rotary evaporation is generally performed at a bath temperature of from 25° C. to 90° C. and a pressure of from 10 mm/Hg to 760 mm/Hg, preferably at a bath temperature of from 40° C. to 90° C. and a pressure from 10 mm/Hg to 350 mm/Hg, more preferably from 40° C. to 60° C. and a pressure of from 10 mm/Hg to 40 mm/Hg. Air drying may be occur at temperatures ranging from 10° C. to 90° C. Rotary evaporation or air drying are generally preferred.

Once obtained, the catalyst precursor is calcined under an inert atmosphere. The inert atmosphere may be any material which is substantially inert, i.e., does not react or interact with, the catalyst precursor. Suitable examples include, without limitation, nitrogen, argon, xenon, helium or mixtures thereof. Preferably, the inert atmosphere is argon or nitrogen, more preferably argon. The inert atmosphere may flow over the surface of the catalyst precursor or may not flow (a static environment). It is important to understand that by non-flow atmosphere is meant that the inert gas is not allowed to flow over the surface of the catalyst precursor. It is preferred that the inert atmosphere not flow over the surface of the catalyst precursor. However, when the inert atmosphere does flow over the surface of the catalyst precursor, the flow rate can vary over a wide range, for example, at a space velocity from 1 to 500 $hr^{-1}$.

The calcination is typically done at a temperature of from 350° C. to 850° C., preferably from 400° C. to 700° C., more preferably from 500° C. to 640° C. The calcination is typically performed for an amount of time suitable to form the catalyst. In one embodiment, the calcination is performed from 0.5 to 30 hours, preferably from 1 to 25 hours and more preferably from 1 to 15 hours.

With calcination a catalyst is formed having the formula

$$A_a M_m N_n X_x O_o$$

wherein A, M, N, and X are as described above. Molar ratios, a, m, n, and x are typically, from $0.25<a<0.98$, $0.003<m<0.5$, $0.003<n<0.5$, and $0.003<x<0.5$; preferably $0.35<a<0.87$, $0.045<m<0.37$, $0.020<n<0.27$, and $0.005<x<0.35$. The catalyst prepared will exhibit at least two crystal phases, one phase including major x-ray diffraction peaks at 22.1, 28.2, 36.2, 45.2, 50.5, 54.2, 55.4, and 58.5, and a second phase including major x-ray diffraction peaks at 22.1, 27.2, 35.3, 45.2, and 51.1. The second phase further includes x-ray diffraction peaks at 7.9, 9.1, and 29.2. Such major peaks and peaks are more completely defined in Table 1 (XRD Peaks of Phase-A) and Table 2 (XRD Peaks of Phase-B) following.

TABLE 1

| diffraction angle(°) | 22.1 | 28.2 | 36.2 | 45.2 | 50.0 | 54.2 | 55.4 | 58.5 |
|---|---|---|---|---|---|---|---|---|
| Relative Intensity | 100 | 80–180 | 5–60 | 2–40 | 2–50 | 2–40 | 2–40 | 2–40 |

TABLE 2

| diffraction angle(°) | 7.9 | 9.1 | 22.1 | 27.2 | 29.2 | 35.3 | 45.2 | 51.1 |
|---|---|---|---|---|---|---|---|---|
| Relative Intensity | 2–30 | 2–30 | 100 | 15–80 | 2–30 | 2–30 | 2–40 | 2–40 |

The molar ratio, "o" i.e., the amount of oxygen (O) present, is dependent on the oxidation state of the other elements in the catalyst. However, typically "o" is from 3 to 4.7, based on the other elements present in the catalyst.

If the composition of the catalyst is varied outside of the ranges defined above, the catalyst will not exhibit both x-ray diffraction phases.

The catalyst of this invention may be used as a solid catalyst alone or may be utilized with a suitable support such as, without limitation, silica, alumina, titania, aluminosilicate, diatomaceous earth, or zirconia. The shape of the catalyst can be any suitable shape and will depend upon the particular application of the catalyst. In a like manner, the particle size of the catalyst may be any suitable particle size depending on the particular use of the catalyst.

In the second aspect of the present invention, there is provided a process for preparing unsaturated aldehydes and acids including subjecting an alkane to catalytic oxidation in the presence of the catalyst described above.

The starting materials for this process are generally an alkane gas or gases and at least one oxygen-containing gas. It is preferred that the starting materials also include steam. Accordingly, a starting material gas is supplied to the system which includes a gas mixture of at least one alkane and steam. The at least one oxygen-containing gas may be included in this mixture or be supplied separately. Furthermore, a diluting gas such as an inert gas including, without limitation, nitrogen, argon, helium, steam, or carbon dioxide may also be included. The diluting gas may be used to dilute the starting material and/or to adjust the space velocity, the oxygen partial pressure, and the steam partial pressure.

Suitable molar ratios of the alkane/oxygen/diluting gas/water in the starting material gas mixture are known in the art as well as the feed ratio of alkane/air/steam. For instance suitable ranges are disclosed in U.S. Pat. No. 5,380,933.

The starting material alkane is generally any alkane suitable for gas phase oxidation into an unsaturated aldehyde or acid. Generally, the alkane is a $C_3$–$C_8$ alkane, preferably propane, isobutane or n-butane, more preferably propane or isobutane, most preferably propane. Furthermore, in another embodiment the alkane may be a mixture of alkanes including $C_3$–$C_8$ alkanes as well as lower alkanes such as methane and ethane.

The at least one oxygen-containing gas used may be pure oxygen gas, an oxygen containing gas such as air, an oxygen enriched gas, or a mixture thereof.

In a preferred embodiment, the starting material is a gas mixture of propane, air, and steam. The starting gas mixture is subjected to catalytic oxidation in the presence of the catalyst of the present invention. The catalyst may be in a fluidized bed or a fixed bed reactor. The reaction is generally conducted under atmospheric pressure, but may be conducted under elevated or reduced pressure. The reaction temperature is generally from 200° C. to 550° C., preferably 300° C. to 480° C., more preferably 350° C. to 440° C. The gas space velocity is generally 100 to 10,000 $hr^{-1}$, preferably 300 to 6,000 $hr^{-1}$, more preferably 300 to 3,000 $hr^{-1}$.

Also, in the method of the present invention it is to be understood that an unsaturated aldehyde may also be formed. For instance when propane is the starting alkane, acrolein may be formed and when isobutane is the starting alkane, methacrolein may be formed.

In the third aspect of the present invention, there is provided a process for preparing unsaturated aldehydes and acids including subjecting a compound selected from propylene, acrolein, and isopropanol to catalytic oxidation in the presence of the catalyst described above. The process is run in the same manner as described above for the conversion of alkanes to unsaturated aldehydes or acids, except propylene, acrolein, or isopropanol is substituted for the alkane. Also, the reaction temperature is generally from 150° C. to 500° C. For propylene and isopropanol the reaction temperature is preferably 250° C. to 400° C., and for acrolein preferably 180° C. to 350° C. The gas space velocity is generally 100 to 10,000 $hr^{-1}$, preferably 300 to 6,000 $hr^{-1}$.

Abbreviations used throughout this application are:

| | | |
|---|---|---|
| ° C. = degrees Centigrade | mm = millimeters | Hg = Mercury |
| g = grams | cm = centimeters | mmole = millimoles |
| % = percent by weight | ml/min = milliliters per minute | |
| $N_2$ = nitrogen | | |

The following examples illustrate the process of the present invention. Based on the amount of starting material used, if there was no compositional segregation, or there was no loss of certain elements during the preparation steps, all of the catalyst samples prepared as follows should have an empirical formula of $Mo_1V_{0.3}Te_{0.23}Nb_{0.08-0.12}O_n$ where n is determined by the oxidation state of the other elements. The solutions or slurries containing the desired metal elements were prepared by heating the appropriate compounds in water at a temperature ranging from 25° C. to 95° C. When necessary, the solutions or slurries were cooled to temperatures ranging from 25° C. to 60° C. The water was then removed from the solutions or slurries by the appropriate drying method at pressures ranging from 760 mm/Hg to 10 mm/Hg.

EXAMPLE 1

A catalyst-1 with the empirical formula of $Mo_1V_{0.3}Te_{0.23}Nb_{0.10}$ was prepared as follows. In a flask containing 420 g of water, 25.8 g of ammonium heptamolybdate tetrahydrate (Aldrich Chemical Company), 5.1 g of ammonium metavanadate (Aldrich Chemical Company) and 7.7 g of telluric acid (Aldrich Chemical Company) were dissolved upon heating to 80° C. After cooling to 40° C., 121.3 g of an aqueous solution of niobium oxalate (Reference Metals Company) containing 17.3 mmole of niobium was mixed to obtain a solution. The water of this solution was removed via a rotary evaporator with a warm water bath at 50° C. and 28 mm/Hg to obtain 46 g of catalyst precursor solid.

Twenty g of the catalyst precursor solid was calcined in a covered crucible pre-purged with argon, in a non-flow environment at 600° C. for 2 hours. The oven had previously been heated to 200° C. and held for one hour, then ramped to 600° C. During the calcination, the covered crucible was in a covered beaker with an Ar space velocity of 57 $hr^{-1}$. Because of the covered crucible, the argon did not flow over the precursor surface, but rather served to insure that the atmosphere outside the crucible remained argon. The atmosphere inside the crucible remained argon and off gasses from the catalyst. The catalyst thus obtained was ground to a fine powder and pressed in a mold and then broken and sieved to 10–20 mesh granules.

The catalyst (13.4 g) was packed into a 1.1 cm inside diameter stainless steel U-tube reactor for gas phase propane oxidation. The oxidation was conducted with a reactor bath (molten salt) temperature of 390° C., a feed ratio of propane/air/steam of 1/15/14, and a space velocity of 1,200 $hr^{-1}$. The effluent from the reactor was condensed to separate the liquid phase (the condensable material) and the gas phase. The gas phase was analyzed by gas chromatography ("GC") to determine the propane conversion. The liquid phase was also analyzed by GC for the yield of acrylic acid. The oxidation results are shown in Table 4. The catalyst was also analyzed by x-ray diffraction to determine its crystalline structure. The main diffraction angles and the corresponding relative intensities are shown in Table 3 and FIG. 1.

EXAMPLE 2

A catalyst-2 with the empirical formula of $Mo_1V_{0.32}Te_{0.23}Nb_{0.08}$ was prepared and tested in the same manner as described in example 1. The oxidation results are shown in Table 4. The main diffraction angles and the corresponding relative intensities are shown in Table 3 and FIG. 1.

EXAMPLE 3

A catalyst-3 with the empirical formula of $Mo_1V_{0.3}Te_{0.2}Nb_{0.1}$ was prepared and tested in the same manner as described in example 1. The oxidation results are shown in Table 4. The main diffraction angles and the corresponding relative intensities are shown in Table 3 and FIG. 1.

g of oxalic acid was mixed to obtain a solution. The solution was dried in the same manner as described in example 1 to obtain a catalyst precursor. The catalyst precursor was pretreated with air at 315° C. for 180 minutes before it was calcined and pressed to granules in the same manner as described in example 1.

One gram of the catalyst was packed into a 3.8 mm inside diameter quartz tube reactor for gas phase propane oxidation. The oxidation was conducted with a reactor bath temperature of 380° C., a feed ratio of propane/air/steam of 1/96/3, and a space velocity of 1,200 hr$^{-1}$. The effluent from the reactor was analyzed by IR to determine the propane conversion and AA yield. The oxidation results are shown in Table 4. The main diffraction angles and the corresponding relative intensities are shown in Table 3 and FIG. 1.

TABLE 3

|        | 7.9° | 9.1° | 22.1° | 27.2° | 28.3° | 29.2 | 35.3 | 36.2° | 45.2° | 50.0° | 51.1 | 54.2 | 554 | 58.5 |
|--------|------|------|-------|-------|-------|------|------|-------|-------|-------|------|------|-----|------|
| Cat. 1 | 13   | 11   | 100   | 37    | 81    | 16   | 15   | 30    | 28    | 25    | 19   | 17   | 16  | 12   |
| Cat. 2 | 11   | 8    | 100   | 30    | 89    | 17   | 10   | 30    | 21    | 22    | 14   | 15   | 18  | 12   |
| Cat. 3 | 14   | 11   | 100   | 39    | 26    | 17   | 13   | 9     | 20    | 11    | 18   | 12   | 8   | 6    |
| Cat. 4 | —    | —    | 100   | —     | 149   |      | —    | 48    | 18    | 41    | —    | 24   | 25  | 19   |
| Cat. 5 | —    | —    | 100   | —     | 169   |      | —    | 59    | 24    | 42    | —    | 27   | 27  | 20   |
| Cat. 6 | —    | —    | 100   | —     | 190   |      | —    | 56    | 21    | 45    | —    | 25   | 25  | 21   |
| Cat. 7 | —    | —    | 100   | —     | 141   |      | —    | 46    | 18    | 38    | —    | 19   | 21  | 18   |

COMPARATIVE EXAMPLE 1

A catalyst-4 with the empirical formula of $Mo_1V_{0.20}Te_{0.40}Nb_{0.05}$ was prepared and tested in the same manner as described in example 1. The oxidation results are shown in Table 4. The main diffraction angles and the corresponding relative intensities are shown in Table 3 and FIG. 1.

COMPARATIVE EXAMPLE 2

A catalyst-5 with the empirical formula of $Mo_1V_{0.31}Te_{0.46}Nb_{0.13}$ was prepared and tested in the same manner as described in example 1. The oxidation results are shown in Table 4. The main diffraction angles and the corresponding relative intensities are shown in Table 3 and FIG. 1.

COMPARATIVE EXAMPLE 3

A catalyst-6 with the empirical formula of $Mo_1V_{0.50}Te_{0.50}Nb_{0.06}$ was prepared and tested in the same manner as described in example 1. The oxidation results are shown in Table 4. The main diffraction angles and the corresponding relative intensities are shown in Table 3 and FIG. 1.

COMPARATIVE EXAMPLE 4

A catalyst-7 with the empirical formula of $Mo_1V_{0.3}Te_{0.23}Nb_{0.10}$ was prepared as follows. In a flask containing 400 g of water, 18.4 g of ammonium heptamolybdate tetrahydrate (Aldrich Chemical Company), 3.7 g of ammonium metavanadate (Aldrich Chemical Company) and 5.5 g of telluric acid (Aldrich Chemical Company) were dissolved upon heating to 80° C. After cooling to 40° C., 75.5 g of an aqueous solution of niobium oxalate (Reference Metals Company) containing 8.0 mmole of niobium and 9.2

The data above demonstrates that both x-ray diffraction phases are present in the catalyst when the catalyst is prepared by the method described above and is within the compositional ranges described above. The catalyst does not exhibit both x-ray diffraction phases when prepared by a different method or when the composition falls outside the range described above.

TABLE 4

| Example | Empirical Formula | Conv. (%) | Sel. (%) | Yield (%) |
|---------|-------------------|-----------|----------|-----------|
| 1       | $Mo_1V_{0.3}Te_{0.23}Nb_{0.10}$  | 73   | 58 | 42  |
| 2       | $Mo_1V_{0.32}Te_{0.23}Nb_{0.08}$ | 78   | 47 | 37  |
| 3       | $Mo_1V_{0.30}Te_{0.20}Nb_{0.10}$ | 43   | 43 | 19  |
| Comp. 1 | $Mo_1V_{0.20}Te_{0.40}Nb_{0.05}$ | 0.6  | 50 | 0.3 |
| Comp. 2 | $Mo_1V_{0.31}Te_{0.46}Nb_{0.13}$ | 11   | 58 | 6.2 |
| Comp. 3 | $Mo_1V_{0.50}Te_{0.50}Nb_{0.06}$ | 6    | 22 | 1.3 |
| Comp. 4 | $Mo_1V_{0.30}Te_{0.23}Nb_{0.10}$ | 49   | 5  | 2.4 |

Comp. = comparative
Conv. (%) = percent of propane converted
Sel. (%) = selectivity of propane conversion to acrylic acid in percent
Yield (%) = the yield of acrylic acid in percent The data above demonstrates that the catalyst is efficient at converting propane to acrylic acid when the catalyst contains both x-ray diffraction phases. The catalyst is ineffective when only one of the x-ray diffraction phases is present in the catalyst.

EXAMPLE 4

Catalyst-2 was tested for oxidation as in example 1, except propylene was substituted for propane. The oxidation was conducted with a reactor bath (molten salt) temperature of 350° C., a feed ratio of propylene/air/steam/nitrogen of 1/35/10/2.8, and a space velocity of 3,600 hr$^{-1}$. The effluent from the reactor was condensed to separate the liquid phase (the condensable material) and the gas phase. The gas phase was analyzed by gas chromatography ("GC") to determine the propylene conversion. The liquid phase was also analyzed by GC for the yield of acrylic acid. The oxidation results are shown in Table 5.

COMPARATIVE EXAMPLE 5

Catalyst-4 was tested in the same manner as described in example 4. The oxidation results are shown in Table 5.

COMPARATIVE EXAMPLE 6

Catalyst-8 with an empirical formula of $Mo_1V_{0.3}Te_{0.23}Nb_{0.10}$ was prepared from the same starting material as described in example 4. A solution containing 39.5 g of ammonium heptamolybdate tetrahydrate, 7.85 g of ammonium metavanadate and 11.8 g of telluric acid and an ammonium niobium oxalate solution containing 27.7 mmole of niobium was prepared in the same manner described in example 1. This solution was frozen to solid form in an acetone-dry-ice bath and dried under vacuum to obtain 64 g of powdery solid. The powdery catalyst precursor was pressed and sized to granules and was calcined at 600° C. for two hours with a steady nitrogen flow.

The resulting catalyst (42 g) was pressed and sized to granules. The catalyst (23 g) was tested in the same way as described in example 4 except at a reactor bath temperature of 390° C. and a feed composition of propylene/air/steam volume ratio at 1/15/14. The oxidation results are shown in Table 5.

TABLE 5

| | Temp. (° C.) | Conv. (%) | Sel. (%) | Yield (%) |
|---|---|---|---|---|
| Example 4 | 350 | 100 | 75.3 | 75.3 |
| Comp. 5 | 350 | 33.2 | 90.7 | 30.1 |
| Comp. 6 | 380 | 46.2 | 83.7 | 38.7 |

Conv. (%) = percent of propylene converted
Temp. = temperature
Sel. (%) = selectivity of propylene conversion to acrylic acid in percent
Yield (%) = the yield of acrylic acid in percent
Comp. = comparative The data above demonstrates that the catalyst is more efficient at converting propylene to acrylic acid when the catalyst contains both x-ray diffraction phases. The catalyst is less effective when only one of the x-ray diffraction phases is present in the catalyst.

EXAMPLE 5

Catalyst-2 was tested for oxidation as in example 1, except isopropanol was substituted for propane. The oxidation was conducted with a reactor bath (molten salt) temperature of 350° C., a feed ratio of isopropanol/air/steam/nitrogen of 1/35/10/2.8, and a space velocity of 3,600 hr$^{-1}$. The effluent from the reactor was condensed to separate the liquid phase (the condensable material) and the gas phase. The gas phase was analyzed by gas chromatography ("GC") to determine the isopropanol conversion. The liquid phase was also analyzed by GC for the yield of acrylic acid. The oxidation results are shown in Table 6.

COMPARATIVE EXAMPLES 7 AND 8

Catalyst-4 was tested in the same way as described in example 5 except at a reactor bath temperatures of both 320° C. and 390° C. and a feed composition of isopropanol/air/steam volume ratio at 1/15/14. The oxidation results are shown in Table 6.

TABLE 6

| | Temp. (° C.) | Conv. (%) | Sel. (%) | Yield (%) |
|---|---|---|---|---|
| Example 5 | 350 | 100 | 49.3 | 49.3 |
| Comp. 7 | 320 | 100 | 18 | 18 |
| Comp. 8 | 390 | 100 | 30 | 30 |

Conv. (%) = percent of isopropanol converted
Temp. = temperature
Sel. (%) = selectivity of isopropanol conversion to acrylic acid in percent
Yield (%) = the yield of acrylic acid in percent
Comp. = comparative The data above demonstrates that the catalyst is more efficient at converting isopropanol to acrylic acid when the catalyst contains both x-ray diffraction phases. The catalyst is less effective when only one of the x-ray diffraction phases is present in the catalyst.

EXAMPLE 6

Catalyst-2 was tested for oxidation as in example 1, except acrolein was substituted for propane. The oxidation was conducted with a reactor bath (molten salt) temperature of 251° C., a feed ratio of acrolein/air/steam of 1.7/52/47, and a space velocity of 3,600 hr$^{-1}$. The effluent from the reactor was condensed to separate the liquid phase (the condensable material) and the gas phase. The gas phase was analyzed by gas chromatography ('GC') to determine the acrolein conversion. The liquid phase was also analyzed by GC for the yield of acrylic acid. The oxidation results are shown in Table 7.

EXAMPLE 7

Catalyst-2 was tested for oxidation as in Example 6, except the oxidation was conducted with a reactor bath (molten salt) temperature of 220° C. The oxidation results are shown in Table 7.

COMPARATIVE EXAMPLES 9 AND 10

Catalyst 4 and catalyst 8 were tested in the same way as described in example 6 except at a reactor bath temperatures of 251° C. and 250° C. respectively and a feed composition of acrolein/air/steam volume ratio at 1/15/14. The oxidation results are shown in Table 7.

TABLE 7

| | Temp. (° C.) | Conv. (%) | Sel. (%) | Yield (%) |
|---|---|---|---|---|
| Example 6 | 251 | 100 | 81.9 | 81.9 |
| Example 7 | 220 | 99.1 | 90.2 | 89.4 |
| Comp. 9 | 251 | 84.6 | 85.5 | 72.3 |
| Comp. 10 | 250 | 97 | 76 | 73.7 |

Conv. (%) = percent of acrolein converted
Temp. = temperature
Sel. (%) = selectivity of acrolein conversion to acrylic acid in percent
Yield (%) = the yield of acrylic acid in percent
Comp. = comparative The data above demonstrates that the catalyst is more efficient at converting acrolein to acrylic acid when the catalyst contains both x-ray diffraction phases. The catalyst is less effective when only one of the x-ray diffraction phases is present in the catalyst.

What is claimed:

1. A process for preparing unsaturated aldehydes and acids comprising subjecting an alkane to catalytic oxidation in the presence of a catalyst comprising:

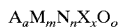

wherein $0.25<a<0.98$, $0.003<m<0.5$, $0.003<n<0.5$, $0.003<x<0.5$, and o is dependent on the oxidation state of the other elements, and A is at least one of Mo, W, Fe, Nb, Ta, Zr, and Ru; M is at least one of V, Ce, and Cr; N is at least one of Te, Bi, Sb, and Se; and X is at least one of Nb, Ta, W, Ti, Al, Zr, Cr, Mn, Fe, Ru, Co, Rh, Ni, Pd, Pt, Sb, Bi, B, In, and Ce; wherein the catalyst exhibits at least two crystal phases, one phase comprising major x-ray diffraction peaks at 22.1, 28.2, 36.2, 45.2, 50.5, 54.2, 55.4, and 58.5, and a second phase comprising major x-ray diffraction peaks at 22.1, 27.2, 35.3, 45.2, and 51.1.

2. The process according to claim 1, wherein the alkane is propane, the unsaturated aldehyde is acrolein.

3. The process according to claim 1, wherein the alkane is propane, the unsaturated acid is acrylic acid.

4. A process for preparing unsaturated aldehydes and acids comprising comprising subjecting a compound selected from propylene, acrolein, and isopropanol to catalytic oxidation in the presence of a catalyst comprising:

wherein $0.25<a<0.98$, $0.003<m<0.5$, $0.003<n<0.5$, $0.003<x<0.5$, and o is dependent on the oxidation state of the other elements, and A is at least one of Mo, W, Fe, Nb, Ta, Zr, and Ru; M is at least one of V, Ce, and Cr; N is at least one of Te, Bi, Sb, and Se; and X is at least one of Nb, Ta, W, Ti, Al, Zr, Cr, Mn, Fe, Ru, Co, Rh, Ni, Pd, Pt, Sb, Bi, B, In, and Ce; wherein the catalyst exhibits at least two crystal phases, one phase comprising major x-ray diffraction peaks at 22.1, 28.2, 36.2, 45.2, 50.5, 54.2, 55.4, and 58.5, and a second phase comprising major x-ray diffraction peaks at 22.1, 27.2, 35.3, 45.2, and 51.1.

5. The process according to claim 4, wherein the compound is propylene and the unsaturated aldehyde is acrolein.

6. The process according to claim 4, wherein the compound is propylene and the unsaturated acid is acrylic acid.

7. The process according to claim 4, wherein the compound is acrolein and the unsaturated acid is acrylic acid.

8. The process according to claim 4, wherein the compound is isopropanol and the unsaturated aldehyde is acrolein.

9. The process according to claim 4, wherein the compound is isopropanol and the unsaturated acid is acrylic acid.

* * * * *